United States Patent [19]

Shinmen et al.

[11] Patent Number: 5,204,250
[45] Date of Patent: Apr. 20, 1993

[54] PROCESS FOR PRODUCTION OF ARACHIDONIC ACID

[75] Inventors: Yoshifumi Shinmen; Hideaki Yamada; Sakayu Shimizu, all of Kyoto, Japan

[73] Assignee: Suntory Limited, Osaka, Japan

[21] Appl. No.: 588,473

[22] Filed: Sep. 26, 1990

Related U.S. Application Data

[63] Continuation of Ser. No. 22,820, Mar. 6, 1987, abandoned.

[30] Foreign Application Priority Data

Mar. 31, 1986 [JP] Japan .................................. 61-71270
Jan. 28, 1987 [JP] Japan .................................. 62-15920

[51] Int. Cl.$^5$ .......................... C12P 7/64; C12P 1/02; C12N 1/38
[52] U.S. Cl. ................................. 435/134; 435/135; 435/244; 435/254; 435/171; 435/911
[58] Field of Search ............... 435/134, 135, 244, 254, 435/171, 911

[56] References Cited

U.S. PATENT DOCUMENTS 4,783,408 11/1988 Suzuki .................................. 435/134

FOREIGN PATENT DOCUMENTS 0155420 9/1985 European Pat. Off. .
0207475 6/1986 European Pat. Off. .
0223960 5/1987 European Pat. Off. .

OTHER PUBLICATIONS

"Production of Arachidonic Acid by *Mortierella elongata* 1S-5" by H. Yamada et al., Agric. Biol. Chem., vol. 51, No. 3, pp. 785-790 (1987).

Agency of Industrial Sciences and Technology, (I) Abstract No. 98: 33069, Chemical Abstracts 1983, p. 537.

Agency of Industrial Sciences and Technology (II) Abstract No. 101:169107, Chemical Abstracts, 1984, p. 539.

"Arachidonic Acid" by H. Iizuka et al., Chemical Abstracts, vol. 87, No. 19, p. 433, Abstract No. 150207h (Nov., 1977).

"Highly Unsaturated Fatty Acie Production by *Euglena*" by M. Okumura et al. Chemical Abstracts, vol. 105, No. 25, p. 625, Abstract No. 224603y, (1986).

"Fermentative Production of γ-Linolenic Acid-Rich Lipids" Agency of Industrial Sciences and Technology, Chemical Abstract vol. 101, No. 19, p. 539, Abstract No. 169107e (1984).

Haskins et al., "Steroids And The Stimulation Of Sexual Reproduction Of A Species Of Pythium", *Canadian Journal of Microbiology*, vol. 10, pp. 187-195 (1964).

Primary Examiner—Irene Marx
Attorney, Agent, or Firm—Burns, Doane, Swecker & Mathis

[57] ABSTRACT

A process for the production of arachidonic acid comprising culturing a microorganism belonging to the genus Mortierella capable of producing arachidonic acid to produce arachidonic acid or a lipid comprising arachidonic acid, and recovering the arachidonic acid.

1 Claim, No Drawings

PROCESS FOR PRODUCTION OF ARACHIDONIC ACID

This application is a continuation of application Ser. No. 07/022,820, filed Mar. 6, 1987 now abandoned.

BACKGROUND OF THE INVENTION

1. Field of the Invention

The present invention relates to a new process for the production of arachidonic acid.

2. Description of the Related Art

Known processes for the production of arachidonic acid are those using microorganisms, i.e., Penicillium, Aspergillus, Rhodotorula or Fusarium, as disclosed in Japanese Examined Patent Publication Nos 56-19231, 56-19232, and 56-19233.

These processes, however, have the disadvantages of a low yield, long term fermentation, and a complicated production process.

However, a process for the production of arachidonic acid using a microorganism belonging to the genus Mortierella is not known.

SUMMARY OF THE INVENTION

Accordingly, the present invention provides a new process for the production of arachidonic acid, comprising culturing a microorganism belonging to the genus Mortierella capable of producing arachidonic acid to produce arachidonic acid or a lipid comprising arachidonic acid, and recovering the arachidonic acid.

DESCRIPTION OF THE PREFERRED EMBODIMENT

In the present invention, as a producer microorganism, any strain belonging to the genus Mortierella capable of producing arachidonic acid can be used. For example, *Mortierella elongata* IFO 8570, *Mortierella exigua* IFO 8571, and *Mortierella hygrophila* IFO 5941 can be used. These strains are stored in the Osaka Institute for Fermentation; 17-85, Juso-honmachi 2-chome, Yodogawa-ku, Osaka 532, Japan, and are available to the public without limitation.

Moreover, a new strain *Mortierella elongata* SAM 0219 can be used. This strain was newly isolated from soil and identified by the present inventor, and was deposited with the Fermentation Research Institute, Agency of Industrial Science and Technology (FRI), Higashi 1-1-3, Yatabe-cho, Tsukuba-gun, Ibaraki-ken, Japan as FERM P-8703 on Mar. 19, 1986, and transferred to International deposition under the Budapest Treaty as FERM BP-1239 on Dec. 22, 1986.

The above-mentioned new strain SAM 0219 (FERM BP-1239) has the following taxonomical properties:

Cultural Characteristics on Various Oulture Media

Culture condition: 25° C. in the dark

1. Malt extract agar medium

Colonies growing fast, attaining a diameter of 28 to 31 mm in two days and a diameter of 65 to 72 mm in five days; colonies are lobed; the formation of aerial mycelium is scanty; sporulation is good; sporangiophores arising from the aerial hyphae; the mycelium has a garlic like odor.

2. Potato dextrose agar medium

Colonies growing fast, attaining a diameter of 27 to 31 mm in two days and a diameter of 75 to 80 mm in five days; colonies form a rosette pattern of dense lobes; much aerial mycelium is formed at the center of the colony; the reverse side of the colony is yellowish white or yellow in color; sporulation is poor; the mycelium has a rather strong garlic-like odor.

3. Czapek's agar medium

Colonies growing moderately fast, attaining a diameter of 22 to 24 mm in two days and a diameter of 50 to 53 mm in five days; the formation of aerial mycelium is scanty; occasionally, the serial hyphae cling tightly to each other; sporulation is abundant; the mycelium has a garlic-like odor.

4. LCA agar medium (prepared according to Koichiro Miura and Mitsuyo Y. Kudo, "An agar-medium for aquatic Hyphomycetes" Transactions of the Mycological Society of Japan vol. 11, p 116–118, 1970)

Colonies growing fast, attaining a diameter of 27-29 mm in two days and a diameter of 64 to 66 mm in five days; colonies are lobed; the formation of aerial mycelium is scanty, except at the center of the colony; sporulation is good; sporangiophores arising from the aerial hyphae; the mycelium has a garlic-like odor.

Microscopic Examination

Sporangiophore, mode of branching sporangiophore, sporangium, sporangiospore, etc., were microscopically observed for microscopic preparations and the colony per se from various media.

A sporangiophore tapers and has a length of 87.5 to 320 $\mu$m, a width of 3 to 7.5 $\mu$m at the root, and a width of 1.0 to 2.5 $\mu$m at the top. A sporangiophore often branches at the root. A sporangium is spherical in form, has a diameter of 15 to 30 $\mu$m, contains many ascospores therein, and has an unclear color after the detaching of the sporangiospore. A sporangiospore is elliptical or, rarely, renal in form, has a smooth surface, and a size of 7.5 to 12.5×5 to 7.5 $\mu$m. A relatively large number of chlamydospores are formed. Chlamydosphores are present separately or, rarely, linked in a chain form. Occasionally, several mycelia appear from the edge of the chlamydosphore. Chlamydosphore is elliptical or subspherical in form, and has a size of 12.5 to 30×7.5 to 15 $\mu$m, or a diameter of 12.5 to 15 $\mu$m. Zygospores are not observed.

Physiological Properties

Optical growth condition:
  pH: 6 to 9,
  Temperature: 20° C. to 30° C.;
Range for growth:
  pH: 4 to 10,
  Temperature: 5° C. to 40° C.

On the basis of the above-mentioned taxonomical properties, and according to J. A. von Arx, "The Genera of Fungi Sporulating in Pure Culture" 3rd ed., J. Cramer, 1981; and K. H. Domsch, W. Gams and T. H. Anderson, "Compendium of Soil Fungi", Academic Press, 1980, the strain SAM-0219 of the present invention is considered to be a fungus belonging to the genus Mortierella, because a sporangium is formed at a top of a sporangiophore, sporangium has no collumella, the sporangiospore has no appendage, and the mycelium has a garlic-like odor.

Therefore, the taxonomical properties of the strain of the present invention was compared with those of known species of the genus Mortierella according to W. Gams, "A key to the species of Mortierella, Persoonia 9: p381-391, 1977. As a result, on the basis of the fact that the colony is not velvety, the mycelium has a garlic-like odor, a sporangiophore has a length of 87.5 to 320 μm, and branches at only its lower part and does not branch racemously, and a sporangium contains many sporangiospore therein, the strain in question was considered to fall under the genus Mortierella, subgenus Mortierella, section Hygrophila. The section Hygrophila includes 22 species. According to a comparison of the present strain with these 22 species, the present strain is similar to *Mortierella zychae*, *M. elongatula*, and *M. elongata*.

Therefore, the strain of the present invention was compared with the above-mentioned three strains, referring to K. H. Domsch, W. Gams, and T.-H. Anderson, "Compendium of Soil Fungi", Academic Press, 1980; W. Gams, "Some New or Noteworthy Species of Mortierella"; Persoonia 9: 111-140, 1976; G. Linnemann, "Mortierella Coemans 1863"; H. Zyche and R. Siepmann, "Mucorales Eine Beschreibung Aller Gattungen und Arten dieser Pilzgruppe", p155-241, J. Cramer, 1965. The present strain is clearly different from *M. zychae* in the length and width of the sporangiophore at the base, and the size of the sporangium. Moreover, the present strain is different from *M. elongatula* in the shape and size of the sporangiospore. The present strain is different from *M. elongata* in that sporangiophore is rather shorter, the chlamydosphore is ellipsoidal or subglobose in form, rarely chlamydospores are linked to each other in a chain form, and give rise to a small number of radiating hyphae. However, the present inventors concluded that such differences between the present strain and *M. elongata* are not sufficient to distinguish the present strain from *M. elongata*, and thus identified the strain of the present invention as *Mortierella elongata*, and designated it as strain SAM 0219.

Spores, mycelia, or a preculture is used as an inoculam for culturing the present strains. The medium used may be a liquid or solid medium. A liquid medium contains as a carbon source, for example, glucose, fructose, xylose, saccharose, maltose, soluble starch, molasses, glycerol, or mannitol. Nitrogen sources include organic substances such as peptones, yeast extract, meat extract, casamino acid, corn steep liquor, and inorganic substances such as sodium nitrate, ammonium nitrate, ammonium sulfate, and the like. If necessary, inorganic salts such as phosphate salts, magnesium sulfate, ferrous sulfate and cupric sulfate, and vitamins may be included in a medium. The concentration of these components is selected so that such components do not adversely affect the growth of the microorganism used. Practically, the concentration of carbon source is 0.1 to 30% by weight, preferably 1 to 10% by weight, reflective to the total weight of the medium. The concentration of the nitrogen source is 0.01 to 5% by weight, preferably 0.1 to 2% by weight, relative to the total weight of the medium.

To enhance the production of arachidonic acid, in addition to the above-mentioned medium components, preferably added to a medium in an amount of 0.01% to 20%. Hydrocarbons are preferably added to a medium at the start of culturing, and fatty acids or salts thereof are preferably added at the start of and/or during culturing. When such an additive is used during culturing, it is added at one time, stepwise, or continuously.

The culturing temperature ranges 5° C. to 40° C., preferably 20° C. to 30° C. A pH value of the medium is 4 to 10, preferably 6 to 9.

Culturing is preferably carried out with aeration and/or agitation, with shaking in a liquid medium, or with standing, and is usually carried out for 2 to 10 days.

When culturing is carried out on a solid medium, the solid medium is composed of wheat bran, chaff or rice bran supplemented with water in an amount of 50 to 100% by weight relative to the wheat bran, chaff or rice bran.

If necessary, the medium is supplemented with a small amount of nitrogen source, inorganic salts, and/or minor nutrients.

Culturing is carried out at a temperature of 5° C. to 40° C., preferably 20° C. to 30° C., for 3 to 14 days.

During culturing, lipids containing arachidonic acid are intracellularly accumulated. When a liquid medium is used, arachidonic acid is recovered from the cultured cells by the following procedure.

After culturing, cultured cells are collected from the cultured broth by a conventional means such as filtration or centrifugation, the cells are washed with water, and preferably, the washed cells are dried. Drying is carried out by, for example, lyophilization or air-drying. The dried cells are treated with an organic solvent or a mixture thereof, preferably under a nitrogen stream, to extract lipid containing arachidonic acid. The organic solvent or mixture thereof is, for example, ethers such as ethyl ether, hydrocarbons such as hexane, alcohols such as methanol or ethanol, halo-hydrocarbon such as chloroform or dichloromethane, petroleum ether, as well as a mixture of chloroform, methanol and water, or a combination of methanol and petroleum ether alternately used. By distilling off the solvent, a lipid containing concentrated arachidonic acid is obtained.

Alternatively, wet cells can be subjected to extraction. In such a case, a water-miscible solvent such as methanol or ethanol, or a water-miscible solvent comprising the water-miscible solvent and water or other organic solvent is used. The extraction procedure is the same as described for dried cells.

The lipid thus obtained contains arachidonic acid in the form of a lipid compound such as fat. Although the arachidonic acid can be isolated in the form of a free acid, it is preferably isolated in the form of an ester with a lower alcohol, for example, as methyl arachidonate. By converting arachidonic acid to such an ester, it is easily separated from other lipid components, and from other fatty acids formed during culturing, such as palmitic acid, oleic acid, linoleic acid and the like, which are also esterified at the same time as the arachidonic acid is esterified. To obtain methyl arachidonate, for example, the lipid prepared as described above is treated with a 5 to 10% hydrochloric acid solution in absolute methanol or a 10 to 50% $BF_3$ solution in methanol for 1 to 24 hours at room temperature.

The mixture thus obtained is extracted with an organic solvent such as hexane, ethyl ether or ethyl acetate, to recover methyl arachidonate. Next, the extract is dried over anhydrous sodium acetate, and the solvent is distilled under reduced pressure to obtain a residue mainly comprising a fatty acid mixture. The mixture contains, in addition to the target compound, methyl arachidonate, methyl palmitate, methyl stearate, methyl oleate and the like. From the mixture, methyl arachidonate is isolated by column chromatography, low temperature crystallization, an urea- adducting method, or a combination thereof.

The isolated methyl arachidonate is then hydrolyzed with an alkali and extracted with an organic solvent such as ethyl ether, ethyl acetate, or the like to obtain a free arachidonic acid.

Alternatively, arachidonic acid can be obtained, without conversion to methyl ester, by alkalolysis with, for example, 5% sodium hydroxide at a room temperature for 2 to 3 hours, followed by extraction of the fatty acids from the alkalolysis product and isolation of the target arachidonic acid.

EXAMPLES

The present invention will now be further illustrated by, but is by no means limited to, the following examples.

EXAMPLE 1

50 ml of a medium containing 5% glucose, 0.5% peptone, 0.3% yeast extract and 0.3% malt extract (pH 6.0) was prepared and charged into a 500 ml-volume Sakaguchi flask, and the whole was autoclaved for 20 minutes at 120° C. After cooling, *Mortierella elongata* SAM 0219 (FERM BP-1239) was inoculated the medium, and then cultured for 5 days at 28° C. with reciprocal shaking at 110 rpm. After culturing, the cultured broth was filtered to recover cells. The cells were then completely washed with water and lyophilized to obtain 1.3 g of dried cells. The cells were extracted with a mixture of chloroform, methanol, and water, according to Bligh and Dyer's one phase extraction method, to obtain 320 mg of a whole lipid. The lipid was treated with a mixture of methanol and hydrochloric acid (95:5) at 20° C. for three hours to esterify the arachidonic acid. The reaction mixture was extracted with ethyl ether to obtain 200 mg of a mixture of fatty acid methyl esters. The mixture contained 9% methyl palmitate, 2% methyl stearate, 32% methyl oleate, 9% methyl linoleate, 10% methyl γ-linolenate. 21% methyl arachidonate, and 17% other components, as determined by gas chromatography. The mixture was separated by column chromatography using octa decylsilane with elution by 95% acetonitrile solution to obtain fractions containing methyl arachidonate. After the fractions were combined, the solvent was distilled off on a rotary evaporator to obtain 25 mg of purified methyl arachidonate. The methyl arachidonate preparation thus obtained was compared with a commmercially available authentic methyl arachidonate preparation, by gas chromatography, high performance liquid chromatography, and mass spectrometry. Both preparations showed the same results, revealing that the preparation prepared in this Example is in fact methyl arachidonate. The amount of methyl arachidonate before and after the purification per cultured broth was 0.84 mg/ml and 0.50 mg/ml respectively; and those per dried cells were 32 mg/g and 19 mg/g respectively.

EXAMPLE 2

5 l of a medium having the same composition as described in Example 1 was charged in a 15 l-volume jar fermenter, and the medium was sterilized at 120° C. for 40 minutes. After cooling, the fermenter was inoculated with 200 ml of a preculture of *Mortierella elongata* SAM 0219 (FERM BP-1239). Culturing was carried out at 30° C. for 3 days with aeration of 0.5 v.v.m. The cultured broth was then filtered to obtain 360 g of wet cells and 4350 l of a filtrate. The cells were dried to obtain 110 g of dried cells. The dried cells thus obtained were subjected to extraction, hydrolysis and methyl-esterification according to the same procedures as described in Example 1, to obtain 29 g of whole lipid containing 18 g of a mixture of fatty acid methyl esters. The mixture contained 8% methyl palmitate, 1% methyl stearate, 29% methyl oleate, 12% methyl linoleate, 11% methyl γ-linolenate, 22% methyl arachidonate, and 17% other components, as determined by the same procedure as described in Example 1. The amount of methyl arachidonate formed was 0.79 g/l broth, and 36 mg/g dried cells.

On the other hand, 4,350 ml of the above-mentioned filtrate was subjected to extraction, hydrolysis and methyl-esterification to obtain 156 mg of a mixture of fatty acid methyl esters including 25% by weight of methyl arachidonate relative to the weight of the mixture.

EXAMPLE 3

The same procedure as described in Example 1 was carried out except that *Mortierella exigua* IFO 8571, and *Mortierella hygrophila* IFO 5941 were used. 72 mg and 95 mg of mixtures of fatty acid methyl esters were obtained respectively, and from these mixtures, 12 mg and 20 mg of methyl arachidonate was isolated and purified, respectively.

EXAMPLE 4

20 ml of a medium containing 2% glucose, 1% yeast extract, and 0.2% Tween 20, as well as an additive, i.e., 0.5% of different kind of hydrocarbons, sodium salt of fatty acid or lipide listed in the following Table 1 (pH 6.0) was charged in each 100 ml-volume Erlenmeyer flask, and the flasks were autoclaved at 120° C. for 20 minutes. *Mortierella elongata* SAM 0219 (FERM BP-1239) was inoculated in the medium and then cultured for 5 days at 28° C. with rotary shaking at 200 rpm. The cultured broths were separately filtered to obtain cells. The cells were then subjected to extraction, hydrolysis, and methyl-esterification according to the same procedure as described in Example 1. The weight of the dried cells, amount of whole lipid, amount of whole fatty acid methyl ester, content of methyl arachidonate, and amount of methyl arachidonate per cultured broth are set forth for each additive.

TABLE 1

| Additive | Weight of dried cells (mg) | Amount of whole lipid (mg) | Amount of whole fatty acid methyl esters (mg) | Content of methyl arachidonate (%) | Amount of methyl arachidonate per broth (mg/ml) |
|---|---|---|---|---|---|
| Octadecane | 330 | 95 | 88 | 20 | 0.88 |
| Sodium oleate | 290 | 81 | 64 | 25 | 0.80 |
| Sodium linoleate | 300 | 96 | 83 | 19 | 0.79 |
| Olive oil | 430 | 130 | 113 | 24 | 1.36 |
| Corn oil | 420 | 118 | 97 | 23 | 1.12 |
| Coconut oil | 380 | 98 | 78 | 25 | 0.98 |
| No addition | 300 | 85 | 68 | 22 | 0.75 |

As seen from the Table 1, the addition of hydrocarbons, salts of fatty acids and lipid increased the production of arachidonic acid by 10 to 80% relative to the no-addition control.

EXAMPLE 5

20 ml of a medium containing 2% glucose and 1% yeast extract was charged in 100 ml-volume Erlenmeyer flasks, and the flasks were autoclaved at 120° C. for 20 minutes. *Mortierella elongata* SAM 0219 (FERM BP-1239) was inoculated in the medium, and then incubated at 28° C. for 4 days. After the addition of 100 mg of a different kind of sodium salt of fatty acid or lipid into each flask, incubation was continued at 28° C. for an additional 2 days. The cultures were separately filtered to obtain cells. The cells were then subjected to extraction, hydrolysis, and methyl-esterification according to the same procedure as described in Example 1. The amount of methyl arachidonate per dried cells and per cultured broth was as set forth for each additive in Table 2.

TABLE 2

| Additive | Amount of methyl arachidonate | |
|---|---|---|
| | mg/g dried cells | mg/ml broth |
| Sodium oleate | 46 | 0.79 |
| Sodium linoleate | 47 | 0.80 |
| Sodium linolenate | 54 | 0.76 |
| Olive oil | 44 | 0.96 |
| Soybean oil | 53 | 1.12 |

TABLE 2-continued

| Additive | Amount of methyl arachidonate | |
|---|---|---|
| | mg/g dried cells | mg/ml broth |
| Linseed oil | 48 | 0.95 |
| No addition | 49 | 0.74 |

As seen from Table 2, the addition of salts of fatty acids and lipids increased the production of arachidonic acid by 10 to 60% relative to the no-addition control.

We claim:

1. A process for producing arachidonic acid or a lipid comprising arachidonic acid, comprising culturing a microorganism selected from the group consisting of *Mortierella elongata* IFO 8570, *Mortierella elongata* SAM 0219 (FERM BP-1239), *Mortierella exigua* IFO 8571, and *Mortierella hygrophila* IFO 5941 wherein culturing is effected in a medium comprising an additive selected from the group consisting of n-hexadecane, n-octadecane, a salt of oleic acid, a salt of linolenic acid, a salt of linoleic acid, olive oil, corn oil, coconut oil, soybean oil and linseed oil, to produce arachidonic acid or a lipid comprising arachidonic acid, and recovering said arachidonic acid or lipid comprising arachidonic acid.

* * * * *